US 6,490,485 B1

(12) United States Patent
Sun et al.

(10) Patent No.: US 6,490,485 B1
(45) Date of Patent: Dec. 3, 2002

(54) AUTOMATIC RATE-ADAPTIVE PACING WITH AUTO-LIFESTYLE

(75) Inventors: Weimin Sun, Plymouth, MN (US); Bruce H. KenKnight, Maple Grove, MN (US); Douglas J. Lang, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/413,663

(22) Filed: Oct. 6, 1999

(51) Int. Cl.⁷ .................................................. A61N 1/365
(52) U.S. Cl. ............................................ 607/20; 607/18
(58) Field of Search ................................ 607/17–20, 27

(56) References Cited

U.S. PATENT DOCUMENTS

| | | | |
|---|---|---|---|
| 4,884,576 A | 12/1989 | Alt | 128/419 PG |
| 4,901,726 A | 2/1990 | Hansen | 128/419 PG |
| 5,044,366 A | 9/1991 | Alt | 128/419 PG |
| 5,226,413 A | 7/1993 | Bennett et al. | 128/419 |
| 5,231,986 A | 8/1993 | Bennett | 607/11 |
| 5,292,340 A * | 3/1994 | Crosby et al. | 607/17 |
| 5,360,436 A | 11/1994 | Alt et al. | 607/18 |
| 5,372,607 A | 12/1994 | Stone et al. | 607/30 |
| 5,376,106 A | 12/1994 | Stahmann et al. | 607/18 |
| 5,476,483 A | 12/1995 | Bornzin et al. | 607/17 |
| 5,487,753 A * | 1/1996 | MacCarter et al. | 607/17 |
| 5,514,162 A * | 5/1996 | Bornzin et al. | 607/19 |
| 5,562,711 A | 10/1996 | Yerich et al. | 607/17 |
| 5,626,622 A | 5/1997 | Cooper | 607/18 |
| 5,645,575 A | 7/1997 | Stangl et al. | 607/17 |
| 5,649,968 A | 7/1997 | Alt et al. | 607/19 |
| 5,690,687 A | 11/1997 | Hansen | 607/17 |
| 5,792,198 A | 8/1998 | Nappholz | 607/18 |
| 5,800,470 A | 9/1998 | Stein et al. | 607/20 |
| 5,843,139 A | 12/1998 | Goedeke et al. | 607/32 |
| 5,931,858 A | 8/1999 | Kadhiresan et al. | 607/20 |
| 5,974,340 A * | 10/1999 | Kadhiresan | 607/18 |
| 5,978,711 A | 11/1999 | van Hove | 607/17 |
| 6,055,454 A * | 4/2000 | Heemels | 607/18 |
| 6,411,850 B1 * | 6/2002 | Kay et al. | 607/19 |

FOREIGN PATENT DOCUMENTS

| | | | |
|---|---|---|---|
| EP | 0798014 | 9/1986 | A61N/1/365 |
| EP | 0702980 | 9/1994 | A61N/1/365 |

* cited by examiner

Primary Examiner—Kennedy Schaetzle
Assistant Examiner—Kristen Droesch
(74) Attorney, Agent, or Firm—Schwegman, Lundberg, Woessner & Kluth, P.A.

(57) ABSTRACT

Methods of adjusting output mapping in response to historical signal input data relative to a reference value, and apparatus to perform the methods. The methods are suited for use in adjusting rate-adaptive pacemakers in response to a patient's demonstrated activity relative to a predetermined activity level. The methods include using historical physiologic sensor input to derive a patient's activity. The methods further include tuning a rate-adaptive curve in response to a demonstrated exertion level and a demonstrated exertion time indicative of a breadth and frequency of a patient's activity above some reference value. Pacemakers adapted to perform the methods include a processor, at least one physiologic sensor, a variable-rate pulse generator and a memory for storing historical physiologic sensor data.

42 Claims, 10 Drawing Sheets

AUTOMATIC RATE-ADAPTIVE PACING WITH AUTO-LIFESTYLE

TECHNICAL FIELD

The invention relates generally to a system for processing sensor input and modifying output mapping and particularly, but not by way of limitation, to methods and apparatus for rate-adaptive pacing responsive to physiologic sensor input.

BACKGROUND

Many control systems rely on an output mapping to convert a measured control input to a desired control output. The output mapping is a graphical, tabular or other mathematical function of control output versus control input. As an example, a burner system with fuel and oxygen feeds may measure fuel feed rate as a control input and utilize output mapping to define the desired oxygen feed rate as a control output. The output mapping of oxygen feed rate versus fuel feed rate may not be linear, e.g., requiring increasing levels of excess oxygen at higher fuel feed rates to provide efficient burning of the fuel. Another example of control systems utilizing output mapping are some cardiac rhythm management systems.

Cardiac rhythm management systems include, among other things, pacemakers, also referred to as pacers. Pacemakers deliver timed sequences of low energy electrical stimuli, called pace pulses, to the heart, such as via a transvenous leadwire having one or more electrodes disposed in the heart. Heart contractions are initiated in response to such pace pulses. By properly timing the delivery of pace pulses, the heart can be induced to contract in proper rhythm, greatly improving its efficiency as a pump. Pacemakers are often used to treat patients with bradyarrhythmias, that is, hearts that beat too slowly, or irregularly.

There exists a class of pacemakers known as variable rate or rate-adaptive pacemakers which include a physiologic sensor indicative of metabolic demand and a variable rate pulse generator responsive to changes in metabolic demand. Some physiologic sensors for determining metabolic demand include minute ventilation (MV) sensors for measuring trans-thoracic impedance variations and generating an output signal varying as a function of the patient's minute ventilation, and accelerometers for measuring body vibration during physical activity and generating an output signal varying as a function of the patient's movement. Accelerometers are typically filtered and processed such that the resulting output signal is indicative of the patient's exercising activity, and not of external vibration sources or internal noise. Other physiologic sensors are known in the art, e.g., blood pH, blood temperature, QT interval, blood oxygen saturation, respiratory rate and others.

Rate-adaptive pacemakers attempt to pace a patient's heart at a rate corresponding to the patient's metabolic demand. They accomplish this by utilizing an output mapping to convert a given sensor input to a unique output signal level. It is difficult to predict an appropriate pacing function capable of generating a paced rate corresponding to a patient's metabolic demand at the time of implanting the pacemaker in the patient. To compensate for this deficiency, rate-adaptive pacemakers may incorporate logic to adjust the output mapping by comparing the patient's average maximum sensor-indicated heart rate (AMSIR) to a sensor target rate (STR) at a prescribed or predetermined level of exercise activity. If the patient's actual or demonstrated activity level differs from the predetermined activity level, the adjusting logic may inappropriately adjust the pacing function, resulting in a paced rate that is too high or too low for a given metabolic demand. If the paced rate is too high, the patient may feel palpitated or stressed. If too low, the patient may feel fatigued, tired or dizzy.

As will be seen from the above concerns, there exists a need for an improved method of adjusting output mapping in response to demonstrated sensor input. The above-mentioned problems with matching pacing to a patient's metabolic demand and other problems are addressed by the present invention and will be understood by reading and studying the following specification.

SUMMARY

One embodiment includes a method of adjusting an output mapping of a control output versus a control input. The method includes obtaining signal input data and generating historical signal input data from the signal input data, wherein the historical signal input data is indicative of a breadth and/or frequency of the signal input data in excess of a reference value. The method further includes adjusting the output mapping in response to the historical signal input data. In another embodiment, the method includes increasing an area of the output mapping in response to increasing values of the breadth and/or frequency of the signal input data in excess of the reference value. In a further embodiment, obtaining signal input data includes obtaining data from the control input and/or from one or more auxiliary inputs.

A further embodiment includes a method of adjusting an output mapping of a control output versus a control input. The method includes obtaining signal input and generating historical signal input data. The method still further includes generating a first factor indicative of a breadth of the historical signal input data in excess of a reference value, generating a second factor indicative of a frequency of the historical signal input data in excess of the reference value, and adjusting the output mapping in response to the first and second factors. In a still further embodiment, adjusting the output mapping further includes increasing an area of the output mapping in response to increasing values of the first factor and decreasing the area of the output mapping in response to decreasing values of the first factor. In yet another embodiment, adjusting the output mapping further includes increasing an area of the output mapping in response to increasing values of the second factor and decreasing an area of the output mapping in response to decreasing values of the second factor. In a further embodiment, obtaining signal input data includes obtaining data from the control input and/or from one or more auxiliary inputs.

Yet another embodiment includes a method of adjusting a rate-adaptive curve for pacing a patient's heart. The method includes sensing the patient's activity, thereby producing sensed activity data, generating a demonstrated activity level from the sensed activity data, and adjusting the rate-adaptive curve in response to the demonstrated activity level relative to a predetermined activity level. In one embodiment, sensing the patient's activity further includes receiving input from at least one physiologic sensor. In another embodiment, sensing the patient's activity further includes receiving input from at least one physiologic sensor including minute ventilation sensors and/or accelerometers. In a further embodiment, adjusting the rate-adaptive curve further includes increasing the rate-adaptive curve when the demonstrated activity level exceeds the predetermined activity level and decreasing the rate-adaptive curve when the demonstrated activity level is less than the predetermined activity level. In a still further embodiment, the predetermined activity level corresponds to a prescribed exercise level and frequency.

One embodiment includes a method of adjusting a rate-adaptive curve for pacing a patient's heart. The method includes sensing the patient's activity having an exertion level, generating a factor indicative of a breadth of the patient's exertion levels above a predetermined exertion level, and adjusting at least a portion of the rate-adaptive curve in response to the factor. In another embodiment, the factor increases for increasing breadth of the patient's exertion levels above the predetermined exertion level.

Another embodiment includes a method of adjusting a rate-adaptive curve for pacing a patient's heart. The method includes sensing the patient's activity having an exertion time at an exertion level, generating a factor indicative of a frequency of the patient's exertion levels above a predetermined exertion level, and adjusting at least a portion of the rate-adaptive curve in response to the factor. In another embodiment, the factor increases for increasing frequency of the patient's exertion levels above the predetermined exertion level.

A further embodiment includes a method of adjusting a rate-adaptive curve for pacing a patient's heart. The method includes sensing the patient's activity having both an exertion level, and an exertion time at the exertion level. The method further includes generating a first factor indicative of a breadth of the patient's exertion levels above a predetermined exertion level, generating a second factor indicative of the patient's exertion time at exertion levels above the predetermined exertion level, and adjusting at least a portion of the rate-adaptive curve in response to the first and second factors. In one embodiment, the first factor increases for increasing breadth of the patient's exertion levels above the predetermined exertion level. In another embodiment, the second factor increases for increasing frequency of the patient's exertion levels above the predetermined exertion level.

A still further embodiment includes a control system. The control system includes a processor, a memory coupled to the processor and having first data stored thereon defining an output mapping, a regulator coupled to the processor, a control input coupled to the processor, and a control output coupled to the regulator. The processor is adapted to sample second data from the control input, store the sampled second data to the memory, thereby generating historical signal input data, and adjust the output mapping in response to the historical signal input data.

Yet another embodiment includes a control system. The control system includes a processor, a memory coupled to the processor, a regulator coupled to the processor, a control input coupled to the processor, at least one auxiliary input coupled to the processor, and a control output coupled to the regulator. The memory has instructions stored thereon capable of causing the processor to perform a method including storing first data to the memory defining an output mapping, sampling second data from the control input, storing the sampled second data to the memory, thereby generating historical control input data, sampling third data from the at least one auxiliary input, and storing the sampled third data to the memory, thereby generating historical auxiliary input data. The method further includes generating a first factor indicative of a breadth of the historical control input data above a first reference value and a breadth of the historical auxiliary input data above a second reference value. The method still further includes generating a second factor indicative of a frequency of the historical control input data above the first reference value and a frequency of the historical auxiliary input data above the second reference value. The method still further includes increasing the output mapping in response to increasing values of the first factor and decreasing the output mapping in response to decreasing values of the first factor, and increasing the output mapping in response to increasing values of the second factor and decreasing the output mapping in response to decreasing values of the second factor.

One embodiment includes a rate-adaptive pacemaker. The rate-adaptive pacemaker includes a processor, a memory coupled to the processor, a variable-rate pulse generator coupled to the processor, and at least one physiologic sensor input coupled to the processor. The memory has instructions stored thereon capable of causing the processor to perform a method including storing first data to the memory defining a rate-adaptive curve, sampling second data from the at least one physiologic sensor input indicative of a patient's activity, storing the sampled second data to the memory, thereby generating historical activity data, and adjusting the first data defining the rate-adaptive curve in response to the historical activity data.

Another embodiment includes a rate-adaptive pacemaker. The rate-adaptive pacemaker includes a processor, a memory coupled to the processor, a variable-rate pulse generator coupled to the processor, and at least one physiologic sensor input coupled to the processor. The memory has instructions stored thereon capable of causing the processor to perform a method including storing first data to the memory defining a rate-adaptive curve, and sampling second data from the at least one physiologic sensor input indicative of a patient's activity having an exertion level and an exertion time at the exertion level. The method further includes storing the sampled second data to the memory, thereby generating historical activity data. The method still further includes generating a first factor indicative of a breadth of the patient's exertion levels above a predetermined exertion level, generating a second factor indicative of the patient's exertion time at exertion levels above the predetermined exertion level, and adjusting at least a portion of the rate-adaptive curve in response to the first and second factors.

The invention further includes other apparatus and methods of varying scope.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the invention. The following detailed description is, therefore, not to be taken in a limiting sense, and the scope of the invention is defined by the appended claims and their equivalents. Like numbers in the figures refer to like components, which should be apparent from the context of use.

The following description will be illustrated in the context of a rate-adaptive pacemaker. Those skilled in the art will recognize that the methods and apparatus described herein can be adapted for use in other systems seeking to modify output mapping in response to demonstrated sensor input relative to a reference value or expected sensor input.

Figure 1:
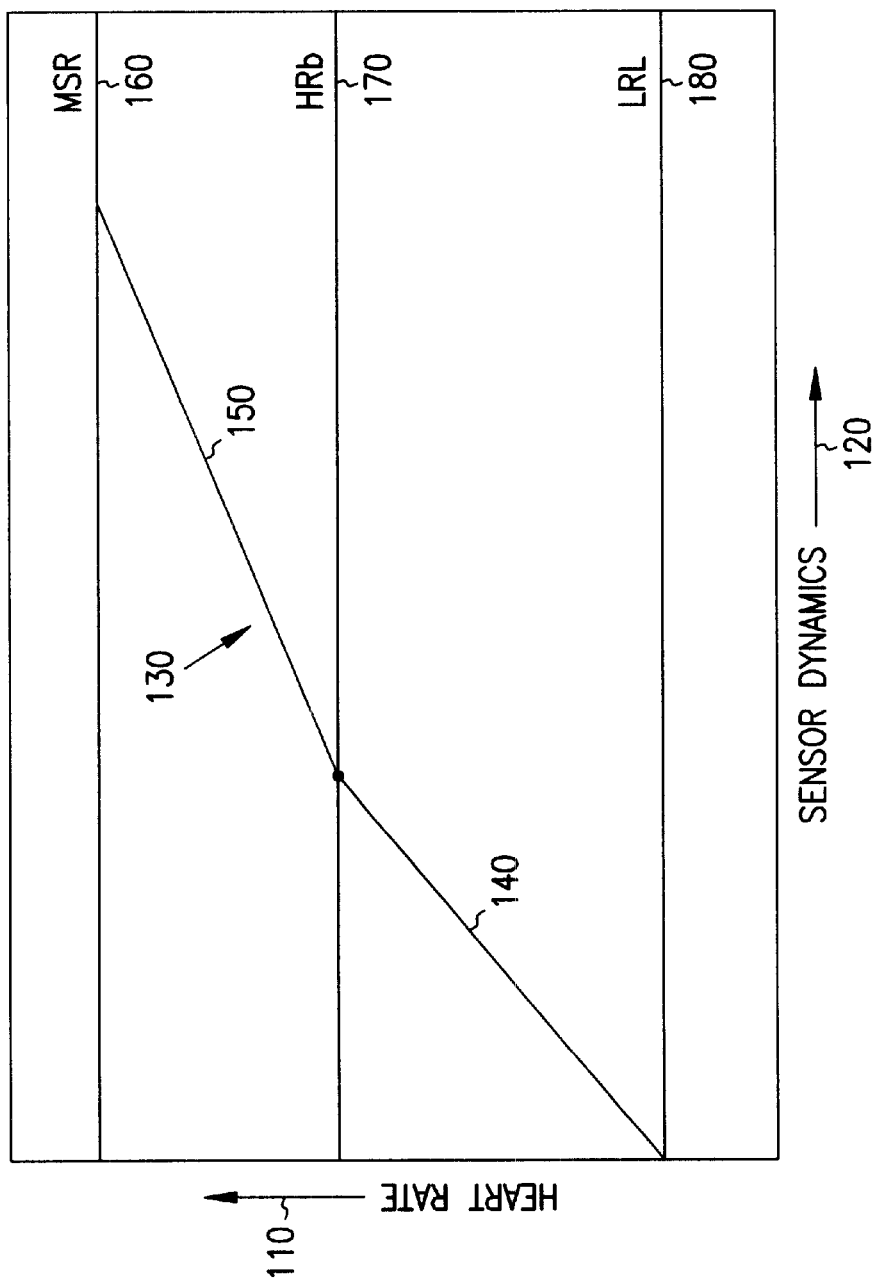
FIG. 1 is a graph of a two-slope rate-adaptive curve.

Current rate-adaptive pacemakers automatically raise the pacing rate, i.e., the control output, of an exercising patient in response to the physiologic sensor, i.e., the control input, often by utilizing an output mapping referred to as a rate-adaptive curve. These rate-adaptive curves may take the form of a two-slope curve. FIG. 1 is graph representative of a two-slope rate-adaptive curve 130, plotting desired heart rate as a function of the physiologic sensor input. In the graph of FIG. 1, heart rate is increasing in the direction of arrow 110 and the sensor signal amplitudes are increasing in the direction of arrow 120. Increasing sensor signal amplitudes are indicative of a higher activity level of the patient.

Rate-adaptive curve 130 includes an aerobic response portion 140 and an anaerobic response portion 150. It is common that the two response portions 140 and 150 meet at the sensor value indicative of the patient reaching the anaerobic threshold, or an activity level where oxygen use exceeds oxygen intake. When using an MV sensor as the physiologic sensor, this point is termed the MV at anaerobic threshold or $MV_{AT}$. The two response portions 140 and 150 further meet at a heart rate at breakpoint or HRb. HRb is shown as line 170 and ideally represents the desired heart rate at the anaerobic threshold. Response portion 140 terminates, or has a lower endpoint, at a lower rate limit (LRL) represented by line 180. LRL is the minimum pacing rate regardless of sensor input. Response portion 150 terminates, or has an upper endpoint, at a maximum sensor rate (MSR) represented by line 160. MSR is the maximum pacing rate driven by sensor input. When using an MV sensor as the physiologic sensor, this endpoint further generally occurs at the peak MV or $MV_{PEAK}$.

Aerobic response portion 140 has a first slope commonly defined by an aerobic response factor (ARF). Anaerobic response portion 150 has a second slope commonly defined by a high heart-rate response factor (HHRRF). Using this two-slope rate-adaptive curve 130, a physiologic sensor input is converted to a desired heart rate or pacing rate. Other forms of rate-adaptive curves, such as linear curves having more or fewer response portions or some non-linear curve, are also capable of performing the output mapping function, i.e., converting a physiologic sensor input into a desired pacing rate. Further, conversion of control input to control output can be accomplished via a look-up table or other non-graphical representation of an output mapping.

Although the various embodiments will be described with reference to a two-slope rate-adaptive curve such as depicted in FIG. 1, the invention is not so limited in its application. Those skilled in the art will recognize that the methods disclosed herein are adaptable to a variety of conversion methods and output mapping curves.

Regardless of the conversion method from sensor input to pacing output, rarely are the patient's actual physiologic dynamics known at the time of implant of the pacemaker. Despite this lack of information, the rate-adaptive curve must be programmed for the pacemaker to function properly, i.e., the MSR, LRL, HRb, ARF and HHRRF have to be specified. In order to tune the rate-adaptive curve to a patient's needs, a sensor target rate (STR) is also specified. The STR represents an expected average maximum sensor-indicated heart rate at the prescribed or predetermined exercise level. The STR is used as a reference by the pacemaker to adjust the response factors, increasing the response of the pacing rate to the physiologic sensor input when the average maximum pacing rate is lower than the STR and decreasing the response of the pacing rate to the physiologic sensor input when the average maximum pacing rate is higher than the STR.

In many systems, the HRb is determined based solely on the patient's age. The STR is determined by an expected average maximum pacing rate based on exercise intensity and exercise frequency which are prescribed by physicians, and programmed into the pacemaker at implant. Both the HRb and STR are generally fixed, unless the pacemaker is reprogrammed. Such systems present limitations. First, the programmed HRb is related to age, but not to a patient's exercise level and capability, i.e., their lifestyle. Whether the patient is sedentary or highly active, HRb remains constant. Second, the programmed STR is based on an exercise level and frequency as prescribed by a physician. This represents the physician's recommendations for exercise level and frequency, but may not match a patient's actual exercise activity and heart demand. Finally, the STR and HRb are not responsive to a patient's activity change, i.e., the response factors are adjusted to match the prescribed STR. Accordingly, the patient will only be paced according to the prescribed STR, regardless of whether the STR prescribed at implant matches the patient's actual heart rate demand.

Differences between the prescribed or predetermined activity level of the patient, and the patient's demonstrated activity level, result in over-responsive or under-responsive pacing. Over-responsive pacing results from a patient demonstrating an activity level below the predetermined activity level and causes the paced heart rate to exceed the metabolic need. Over-responsive pacing generally results in a patient experiencing palpitation or stress. Under-responsive pacing results from a patient demonstrating an activity level exceeding the predetermined activity level and causes a deficit between the paced heart rate and the metabolic need. Under-responsive pacing generally results in a patient experiencing fatigue, tiredness or dizziness.

Figure 2:
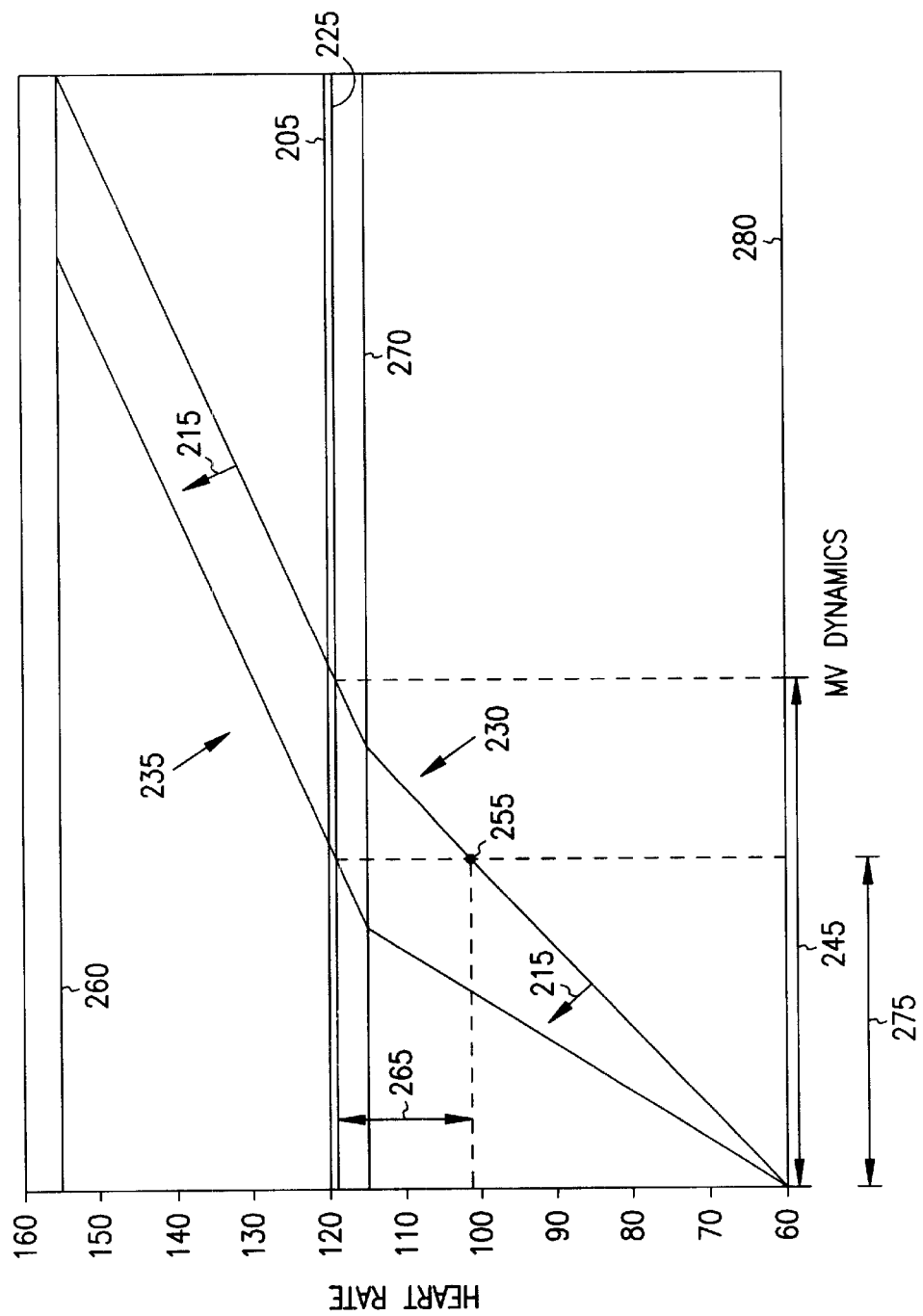
FIG. 2 is a graph of a two-slope rate-adaptive curve depicting over-responsive pacing.

FIG. 2 is a graph depicting the tuning of a rate-adaptive curve 230 resulting in over-responsive pacing. FIG. 2 includes MSR 260, LRL 280 and HRb 270. FIG. 2 further includes a target heart rate at exercise, or TR 205, and STR 225. TR 205 represents a prescribed or predetermined heart rate during exercise. STR 225 represents the expected average maximum sensor-indicated heart rate at the predetermined activity level of the patient. The predetermined activity level is represented by the predetermined average MV dynamics 245, i.e., the expected average MV dynamics should the patient exercise at the prescribed intensity and frequency. Increasing predetermined activity level, e.g., prescribing a higher frequency of exercise, results in STR 225 approaching TR 205.

FIG. 2 may represent data of a 65-year old patient with a high predetermined activity level. If the patient's demonstrated activity, represented by the demonstrated average MV dynamics 275, is less than the predetermined activity level, tuning of rate-adaptive curve 230 based on the patient's average paced maximum rate in comparison to STR 225 results in an over-responsive pacing situation. This result is caused by the false assumption that the patient's demonstrated activity matches their predetermined activity level. Because the patient's predetermined average MV dynamics 245 exceeds their demonstrated average MV dynamics 275, STR 225 will exceed the patient's average paced maximum rate 255 by the span 265. In response, rate-adaptive curve 230 will be increased in the direction of arrows 215 to yield rate-adaptive curve 235. An output mapping is increased when its area is increased, i.e., the average of the control output values across the range of possible control input values is increased. Thus, a rate-adaptive curve is increased when the area under the rate-adaptive curve is increased. Tuning rate-adaptive curve 230 to yield rate-adaptive curve 235 may include modifying the slopes of the response portions, as well as the intersection of the response portions. Rate-adaptive curve 235, having been formed on the false assumption that the patient's demonstrated activity matches their predetermined activity level, paces the patient's heart at a rate exceeding metabolic need.

Figure 3:
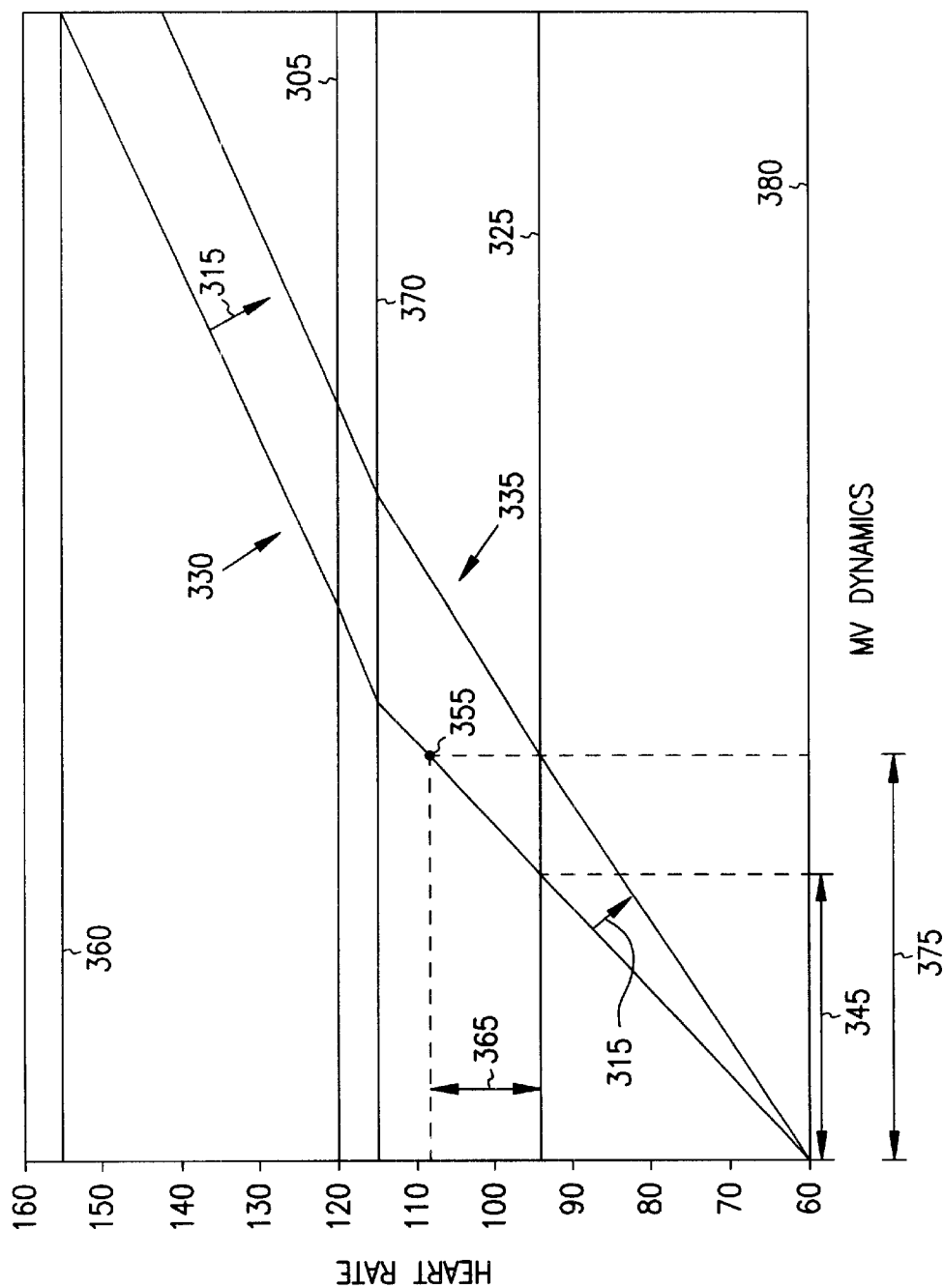
FIG. 3 is a graph of a two-slope rate-adaptive curve depicting under-responsive pacing.

FIG. 3 is a graph depicting the tuning of a rate-adaptive curve 330 resulting in under-responsive pacing. FIG. 3 includes MSR 360, LRL 380 and HRb 370. FIG. 3 further includes a target heart rate at exercise, or TR 305, and STR 325. TR 305 represents a prescribed or predetermined heart rate during exercise. STR 325 represents an expected average maximum sensor-indicated heart rate at the predetermined activity level of the patient. The predetermined activity level is represented by the predetermined average MV dynamics 345, i.e., the expected average MV dynamics should the patient exercise at the prescribed intensity and frequency. Decreasing predetermined activity, e.g., prescribing a lower frequency of exercise, results in STR 325 receding from TR 305.

FIG. 3 may represent data of a 65-year old patient with a low predetermined activity level. If the patient's demonstrated activity, represented by the demonstrated average MV dynamics 375, is greater than the predetermined activity level, tuning of rate-adaptive curve 330 based on the patient's average paced maximum rate in comparison to STR 325 results in an under-responsive pacing situation. This result is caused by the false assumption that the patient's demonstrated activity matches their predetermined activity level. Because the patient's demonstrated average MV dynamics 375 exceeds their predetermined average MV dynamics 345, the patient's average paced maximum rate 355 will exceed STR 325 by the span 365. In response, rate-adaptive curve 330 will be decreased in the direction of arrows 315 to yield rate-adaptive curve 335. An output mapping is decreased when its area is decreased, i.e., the average of the control output values across the range of possible control input values is decreased. Thus, a rate-adaptive curve is decreased when the area under the rate-adaptive curve is decreased. Tuning rate-adaptive curve 330 to yield rate-adaptive curve 335 may include modifying the slopes of the response portions, as well as the intersection of the response portions. Rate-adaptive curve 335, having been formed on the false assumption that the patient's demonstrated activity matches their predetermined activity level, paces the patient's heart at a rate less than their metabolic need.

In one embodiment, historical data from a physiologic sensor is collected over a period of time. The period of time over which data is collected as well as the collection frequency of capturing an individual data point can be of any value, limited only by available memory capacity. As a practical matter, the period of time may often be a day, a week or a month while the collection frequency may be from 1 to 4 data points per minute. In one embodiment, the physiologic sensor is a control input. In another embodiment, the physiologic sensor is an auxiliary input.

Figure 4A:
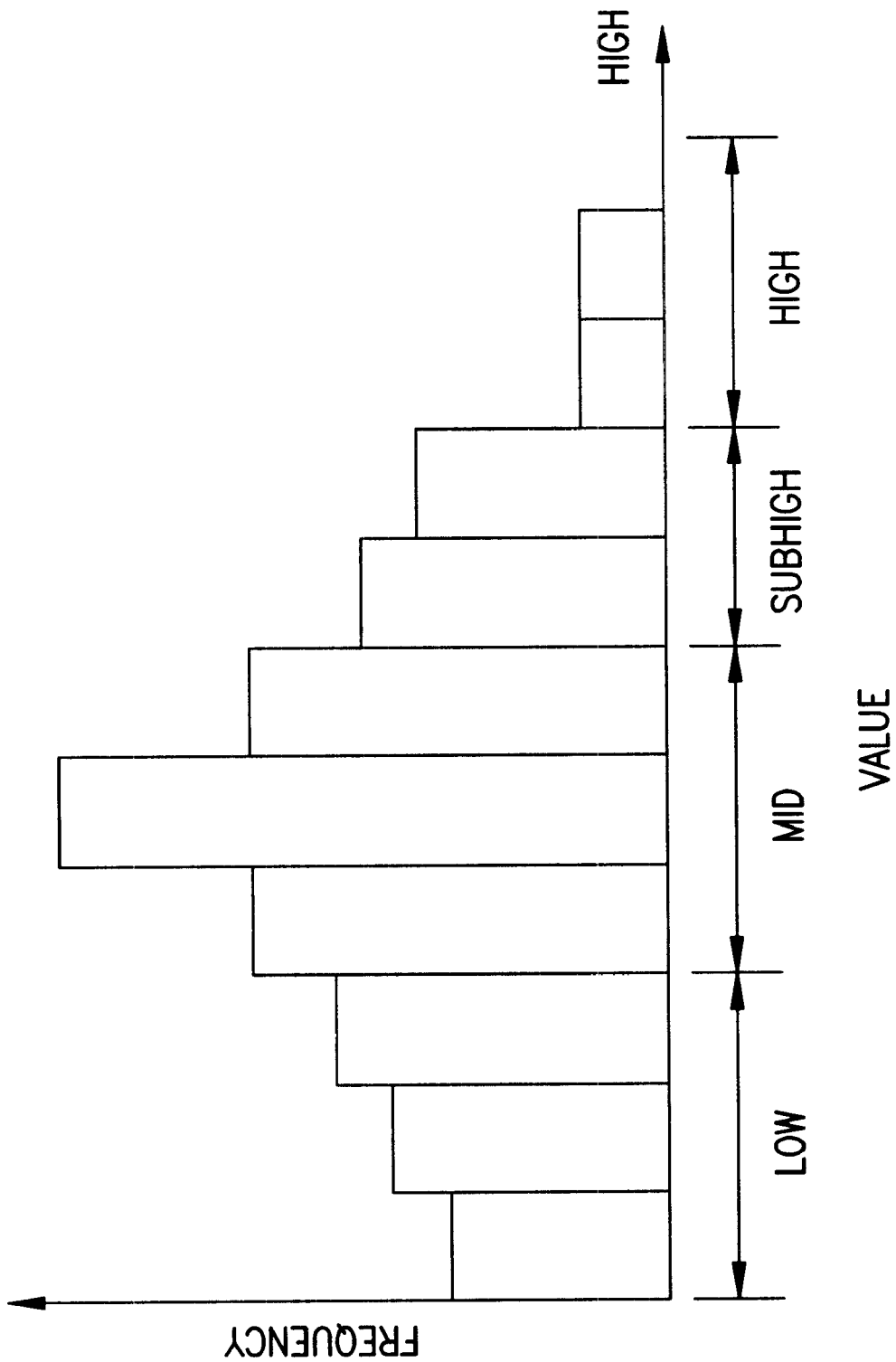
FIGS. 4A–4C are histograms of exemplary physiologic sensor data.

The historical data from the physiologic sensor is indicative of a patient's activity over the period of time. If plotted as a histogram, each bar is indicative of an activity level while the area of the bar is indicative of duration of time at that activity level. FIG. 4A is a histogram of a set of hypothetical physiologic sensor data. Each bar could represent a discrete sensor value, or it could represent a range of sensor values. The physiologic sensor may be an MV sensor, an accelerometer or other sensor previously described.

The bars or bins of the histogram of FIG. 4A are further grouped as "Low," "Mid," "Sub-High" and "High." Low values may be indicative of a patient at rest. Mid values may be indicative of a patient performing normal activities such as walking at a relaxed pace. Sub-High values may be indicative of a patient involved in aerobic exercise or activities. High values may be indicative of a patient involved in strenuous exercise or activities. These designations and groupings are by way of example only, and not by limitation.

Increasing the number of groupings or bins and/or increasing the length of time represented by the historical data tend to improve accuracy of tuning the rate-adaptive curve. However, this improved accuracy comes at the price of additional memory or storage requirements, and additional computation time and complexity.

Figure 4B:
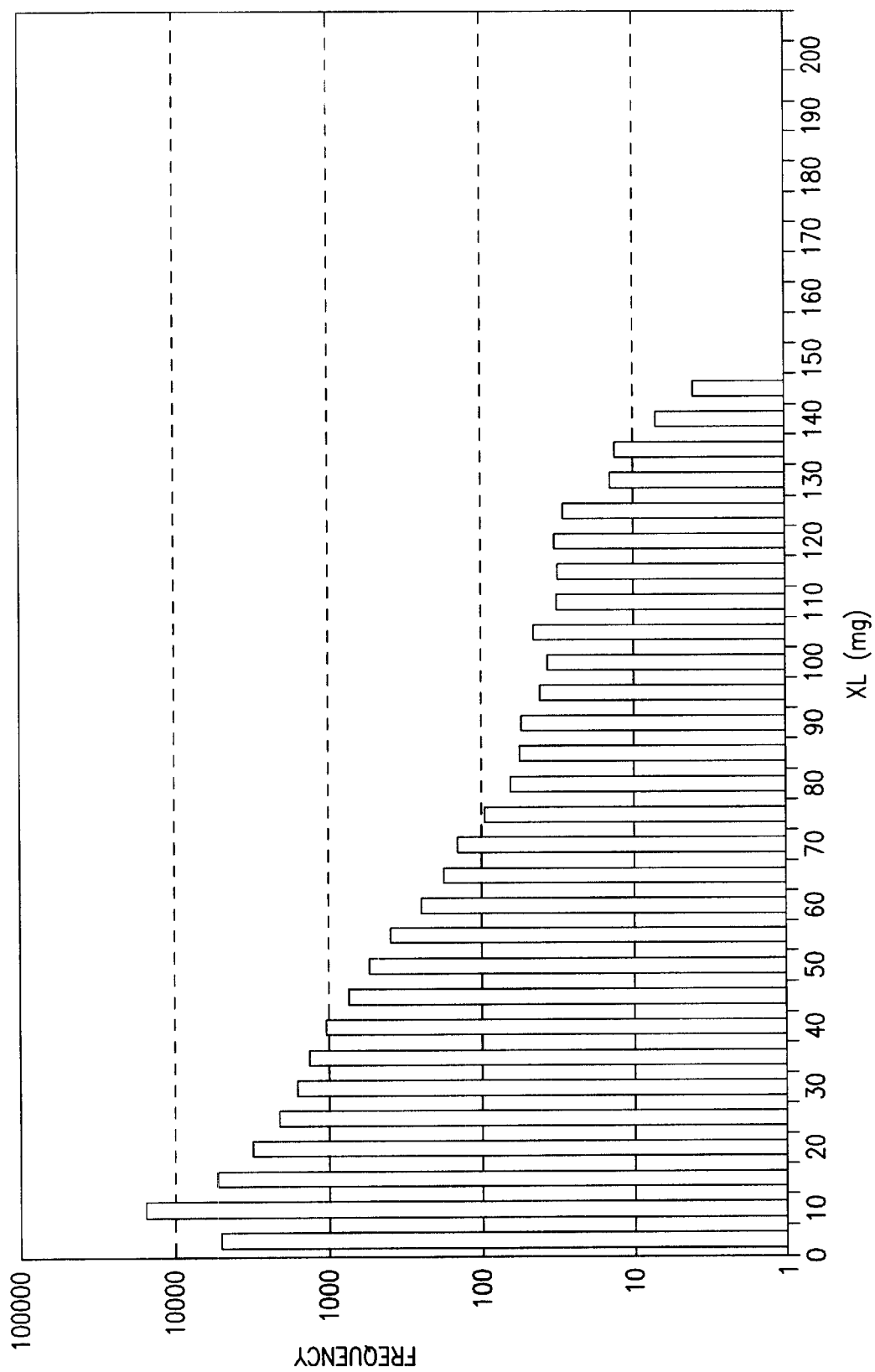
Figure 4C:
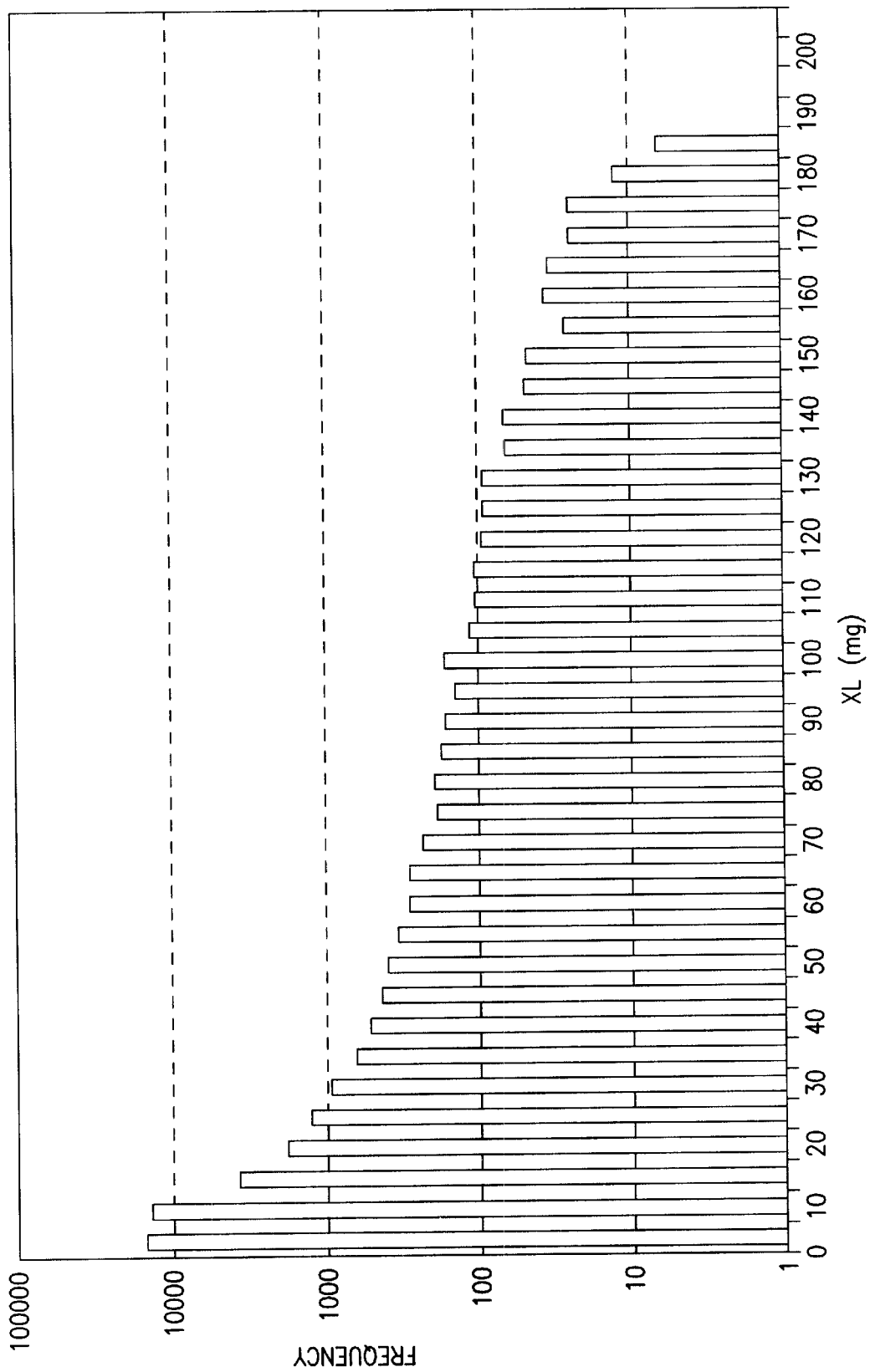

FIGS. 4B and 4C are histograms of accelerometer data that are generally representative of two different lifestyles. FIG. 4B is generally representative of a person having a rather sedentary lifestyle. FIG. 4C is generally representative of a person having a more active lifestyle.

The historical data can be evaluated to derive the patient's demonstrated activity. In one embodiment, demonstrated activity is derived from the historical data of a physiologic sensor as a control input. In another embodiment, demonstrated activity is derived from the historical data of a physiologic sensor as an auxiliary input. In a further embodiment, demonstrated activity is derived from the historical data of more than one physiologic sensor, i.e., a control input and one or more auxiliary inputs. In a still further embodiment, demonstrated activity is derived from the historical data of an MV sensor and/or an accelerometer.

In one embodiment, the patient's demonstrated activity, or lifestyle, is expressed as a function of two parameters representing an exertion time, LSet, and an exertion level, LSel. LSet is indicative of how long a patient exercised during the period of time for collecting the historical data. LSel is indicative of how hard a patient exercised during the period of time. LSet and LSel are utilized to evaluate whether and to what extent the rate-adaptive curve should be tuned. Increasing breadth of physiologic sensor input values above some physiologic sensor reference point, e.g., expected sensor input at moderate activity or prescribed activity, leads to increasing values of LSel. Increasing area or frequency of physiologic sensor input values above the physiologic sensor reference point leads to increasing values of LSet.

Figure 5:
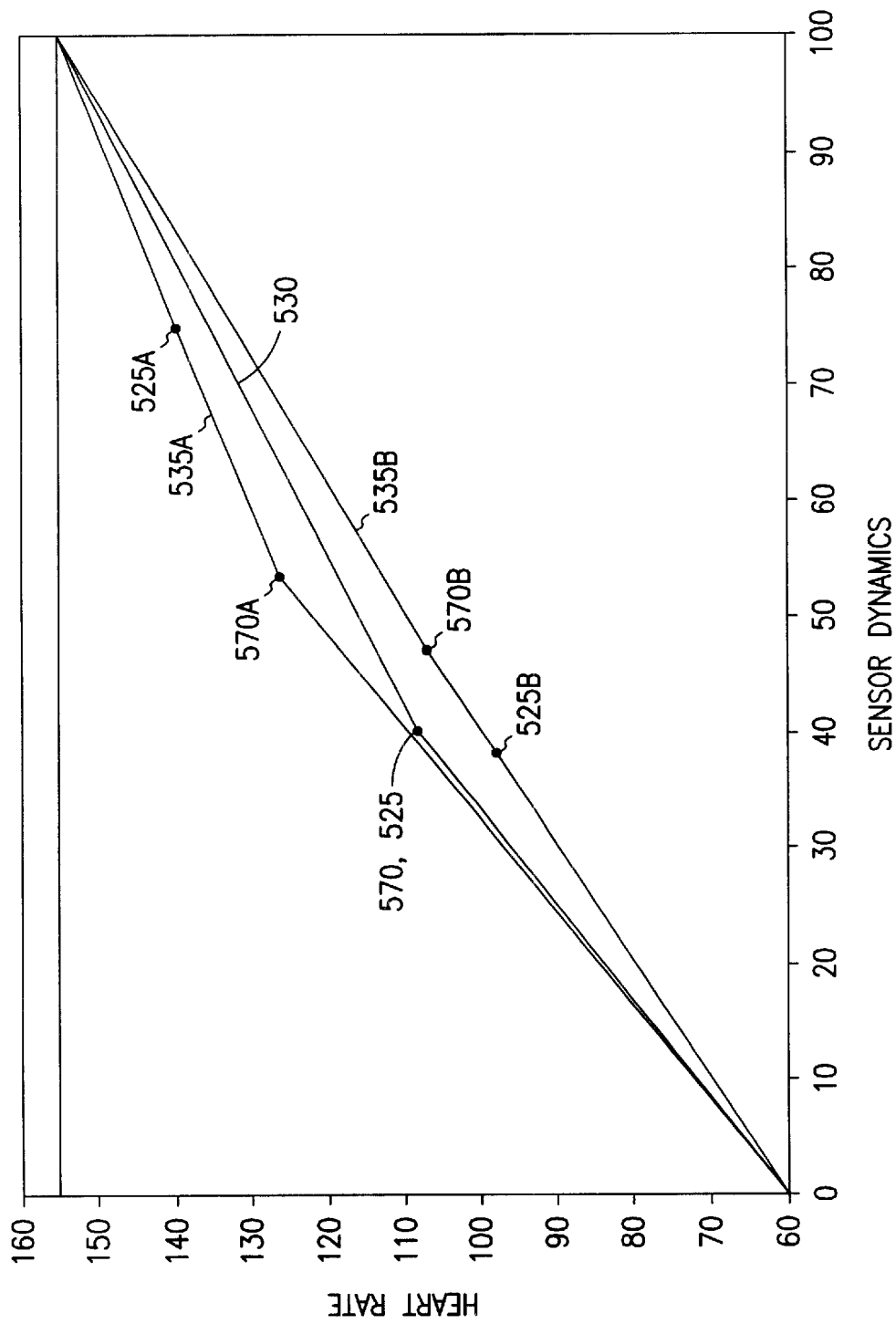
FIG. 5 is a graph of a two-slope rate-adaptive curve depicting tuning in response to a patient's demonstrated activity.

This historical data of patient activity can be applied in a multitude of variations in light of the general guidance provided above. The two-slope rate adaptive curve will be used to demonstrate an example embodiment of the application of the historical data for tuning of the rate-adaptive curve. In this embodiment, the pacemaker is first programmed with its MSR, LRL, HRb, ARF, HHRRF and STR as is typical in such devices. FIG. 5, may represent data of a 65-year old patient. The scale of the sensor dynamics is nominally 0–100 to correspond to the range of the LRL to the MSR; it does not represent absolute sensor input. Furthermore, the sensor dynamics may relate to an MV sensor or other physiologic sensor indicative of metabolic demand.

The pacemaker has an initial rate-adaptive curve 530 for a moderate activity level. In this case, MSR equals 220 minus the age, or 155. LRL equals 60. HRb is set to 0.7 times MSR, or 108.5. The aerobic response portion of rate-adaptive curve 530 has an initial slope of approximately 1.2 and the anaerobic response portion of rate-adaptive curve 530 has an initial slope of approximately 0.67 in this example.

The slopes of the aerobic and anaerobic response portions are generally determined by setting ARF and HHRRF in a pacemaker, and ARF and HHRRF may have discrete values characteristic of the pacemaker. For example, ARF may have 16 discrete values ranging from 0 to 15, and a setting of 8 may result in the desired slope for the aerobic response portion.

The STR has been set to equal HRb. STR is depicted as point 525. HRb is depicted as point 570, which in rate-adaptive curve 530 is the same point as STR point 525.

For tuning the rate-adaptive curve 530 to the patient's lifestyle, the variables HRb, STR, ARF and HHRRF may be redefined in response to the demonstrated activity. In one embodiment, three of the variables are redefined in response to the demonstrated activity while the fourth is defined by system constraints such as defined curve endpoints or a decision based on the STR compared to the average maximum sensor-indicated heart rate.

In one embodiment, HRb, STR and HHRRF are redefined in response to the demonstrated activity while the aerobic response portion of the rate-adaptive curve is constrained by the endpoints of the initial rate-adaptive curve 530. In a further embodiment, HRb, STR and HHRRF are redefined as a function of at least one of the exertion level and the exertion time of the patient. In a still further embodiment, HRb and HHRRF are redefined in proportion to the exertion level, while STR is redefined in proportion to the exertion level and the exertion time.

In yet another embodiment, HRb, STR and HHRRF are redefined according to the following functions:

$HRb = LRL + (MSR-LRL)*(N_1 + N_2 * LSel)$ $STR = LRL + (HRb-LRL)*(N_3 + N_4 * LSel + N_5 * LSet)$ $HHRRF = N_6 - N_7 * LSel$ where: $N_1$ through $N_7$ are empirical constants and LSel and LSet are empirical variables such that only minimal or insubstantial corrections are applied when the patient's demonstrated exertion time and level are substantially equal to the prescribed exertion time and level, HRb and HHRRF are generally increased in response to exertion levels above the prescribed exertion level and generally decreased in response to exertion levels below the prescribed exertion level, and STR is generally increased in response to exertion times and levels above the prescribed exertion time and level and generally decreased in response to exertion times and levels below the prescribed exertion time and level.

In a further embodiment, HRb, STR and HHRRF are redefined according to the following functions:

$HRb = LRL + (MSR-LRL)*(0.6 + 0.1 * LSel)$ $STR\ 32\ LRL + (HRb-LRL)*(1 + 0.1 * LSel + 0.1 * LSet)$ $HHRRF = 0.7 - 0.1 * LSel$ where:
LSel is an integer value between –2 and +1
LSet is an integer value between –2 and +1

By constraining the foregoing equations to the endpoints of the initial rate-adaptive curve 530, i.e., LRL and MSR, the slope of the aerobic response portion may be calculated from the known values of HRb, STR, HHRRF.

As an example, rate-adaptive curve 530 may be tuned in response to the patient demonstrating an activity level above the nominal values programmed initially into the pacemaker, i.e., the predetermined activity level. LSel and LSet may be set to +1 to indicate that the patient's demonstrated activity exceeds their predetermined activity level. There is no limitation that both LSel and LSet be set to the same value as both are independently adjustable. Rate-adaptive curve 535A represents the tuning of rate-adaptive curve 530 in response to the increased activity according to the preceding equations.

As a further example, rate-adaptive curve 530 may be tuned in response to the patient demonstrating an activity level below the nominal values programmed initially into the pacemaker, i.e., the predetermined activity level. LSel and LSet may be set to –1 to indicate that the patient's predetermined activity level exceeds their demonstrated activity. There is no limitation that both LSel and LSet be set to the same value as both are independently adjustable. Rate-adaptive curve 535B represents the tuning of rate-adaptive curve 530 in response to the decreased activity according to the preceding equations.

As a variation, the equations could be constrained to having the STR equal the average maximum sensor-indicated heart rate while allowing one of the endpoints to be variable, e.g., the lower endpoint where STR is less than HRb and the upper endpoint where STR is greater than HRb. While these examples are illustrative of the use of the historical activity data, they are by no means exhaustive. In each case, however, the use of historical activity data provides for a more objective tuning of the rate-adaptive curve than is possible in responding to average maximum sensor-indicated heart rate alone. Furthermore, the use of historical activity data provides for a more objective tuning of any method of converting physiologic sensor input to desired pacing rate than is possible in responding to average maximum sensor-indicated heart rate alone.

In addition, further tuning algorithms may be applied in addition to the tuning in response to the patient's demonstrated activity. For example, following adjustment of the rate-adaptive curve 530 to one of rate-adaptive curves 535A and 535B, further adjustments could be made as described with reference to FIG. 2 or 3.

Figure 6:
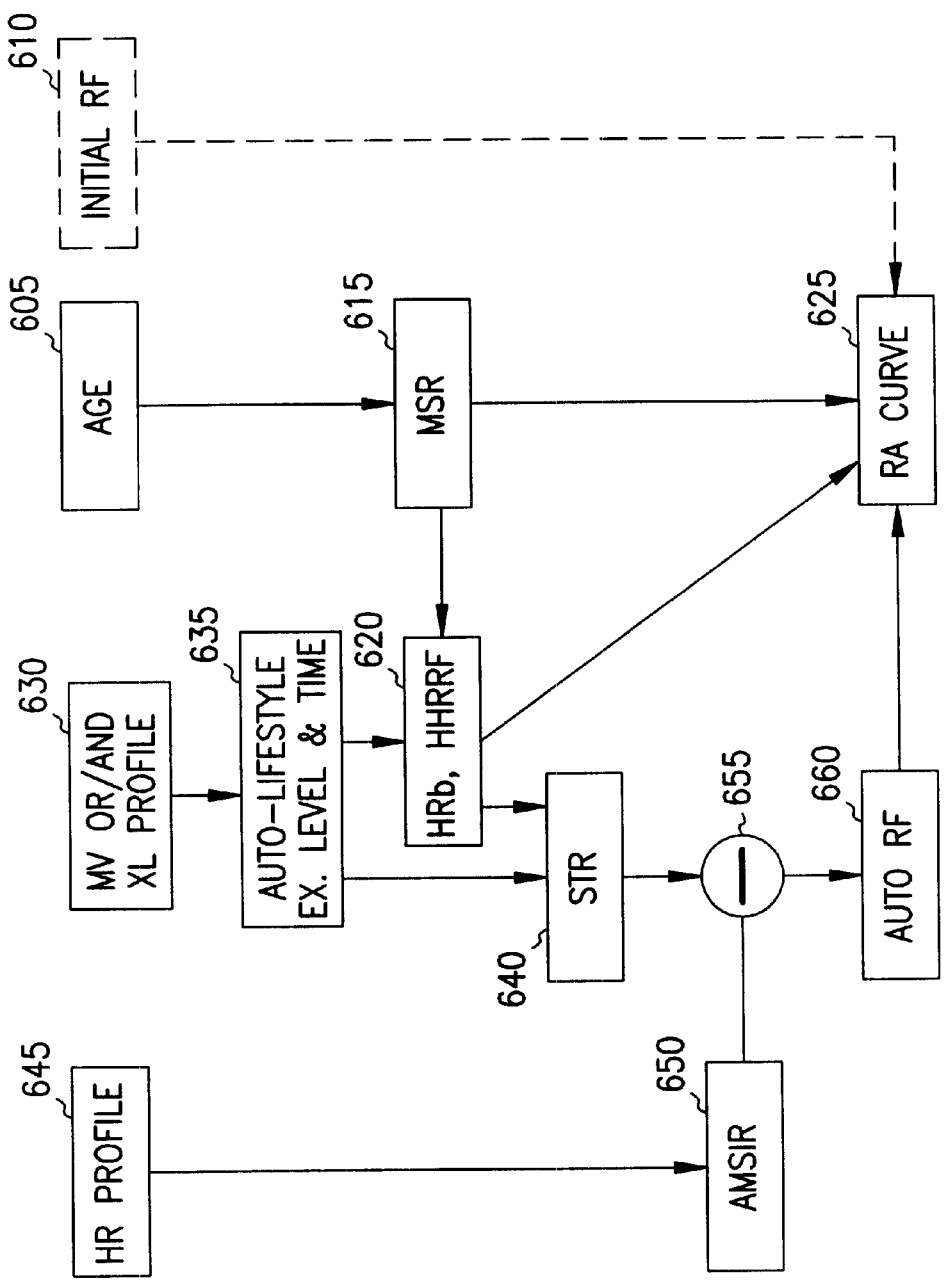
FIG. 6 is a flowchart of a method of tuning a rate-adaptive curve.

FIG. 6 is a flowchart depicting one embodiment of a method of tuning a rate-adaptive curve in a pacemaker. The age of a patient if provided at box 605 and used to define a maximum sensor rate at box 615. The maximum sensor rate at box 615 is used as input to box 625, as part of the tuning of the rate-adaptive curve, and to box 620, as part of redefining the heart rate at breakpoint and the high heart-rate response factor. An initial response factor is provided at box 610 as part of the initial definition of the rate-adaptive curve in box 625. Box 610 and its connection to box 625 are shown in broken lines as the initial response factor is used in the definition of the rate-adaptive curve only at programming, and is not involved in subsequent redefinition of the rate-adaptive curve.

Data from minute ventilation and/or accelerometer sensors is measured by the pacemaker, and historical data is stored, in box 630. The historical data from box 630 is used as input to box 635 to generate factors indicative of exertion level and exertion time of the patient. One or more factors from box 635 are provided to box 620, as part of redefining the heart rate at breakpoint and the high heart-rate response factor, and to box 640, as part of redefining the sensor target rate. The heart rate at breakpoint from box 620 is also provided to box 640 as part of redefining the sensor target rate.

In box 645, the patient's heart rate profile is measured, and historical data is stored, as input to box 650 in the generation of an average maximum sensor-indicated heart rate. The sensor target rate of box 640 is compared with the average maximum sensor-indicated heart rate of box 650 in comparison block 655 to generate an new response factor in box 660. This comparison can take the form of the comparisons as detailed with reference to FIGS. 2 and 3. The new response factor from box 660 is combined with the heart rate at breakpoint and high heart-rate response factor from box 620 and the maximum sensor rate from box 615 to tune the rate-adaptive curve in box 625.

Figure 7:
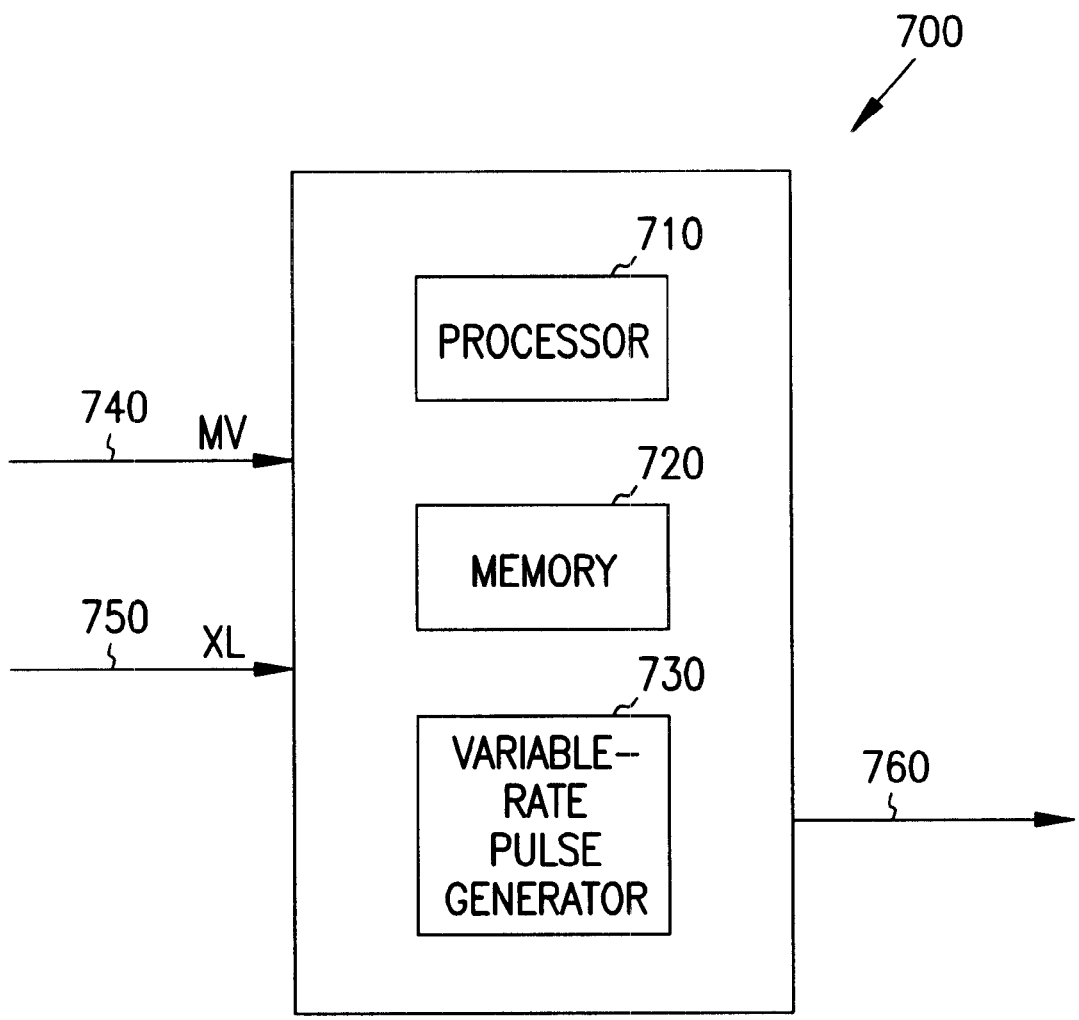
FIG. 7 is a block diagram of a pacemaker.

A pacemaker 700 adapted to perform methods of the invention is depicted in FIG. 7. It will be recognized by those skilled in the art that pacemaker 700 may include other components, but that FIG. 7 has been simplified to focus on the invention. Pacemaker 700 includes a processor 710, a memory 720 coupled to processor 710, and a variable-rate pulse generator 730, or regulator, coupled to processor 710. Pacemaker 700 further includes a first physiologic sensor input 740, in this example an MV sensor input, and optionally a second physiologic sensor input 750, in this example an accelerometer. First physiologic sensor input 740 is a control input. Second physiologic sensor input 750 is an auxiliary input. To provide the pacing to the patient's heart, pacemaker 700 also includes a pulse output 760.

Memory 720 provides storage for the historical data as well as data capable of defining the output mapping responsive to the control input. In one embodiment, the output mapping includes a rate-adaptive curve defined by factors such as HRb, aerobic response factor and high heart-rate response factor. Memory 720 is generally some form of machine-readable medium such as random-access memory (RAM), read-only memory (ROM) or flash memory. Memory 720 further contains instructions stored thereon capable of causing processor 710 to carry out the methods of the invention.

Processor 710 receives input from sensor inputs 740 and 750. Processor 710 samples, processes and stores the historical data in memory 720. Processor 710 tunes the data defining the rate-adaptive curve at least in response to the historical data from at least one sensor input, where that historical data is indicative of the patient's activity. Processor 710 further utilizes the first physiologic sensor input 740 and the data defining the rate-adaptive curve to cause variable-rate pulse generator 730 to generate a signal on pulse output 760, thus providing desired pacing to the patient's heart.

Figure 8:
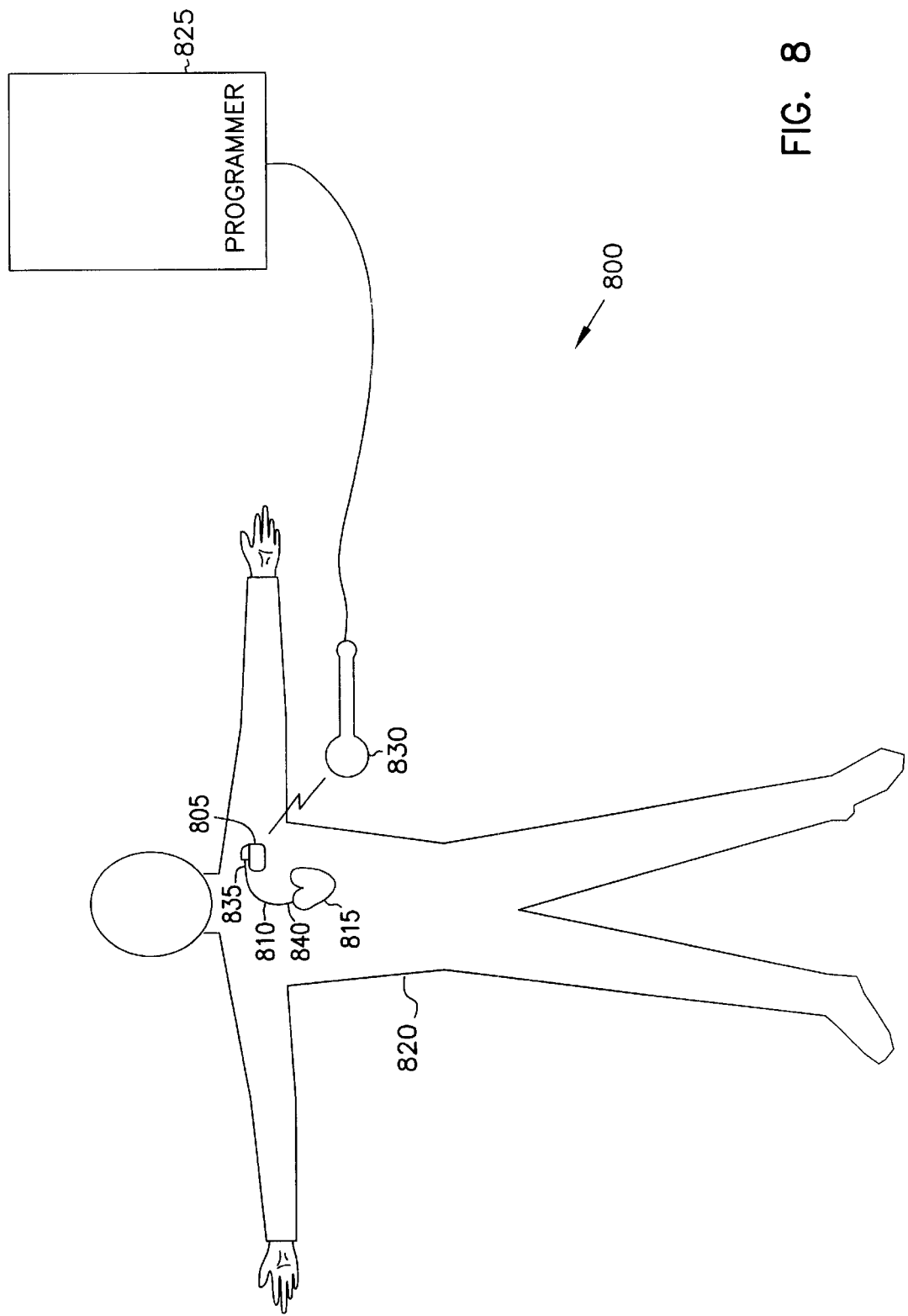
FIG. 8 is a schematic of a cardiac rhythm management system and an environment in which it is used.

FIG. 8 is a schematic drawing illustrating, by way of example, but not by way of limitation, one embodiment of portions of a cardiac rhythm management system 800 and an environment in which it is used. In FIG. 8, system 800 includes an implantable pacemaker 805, also referred to as an electronics unit, which is coupled by an intravascular endocardial lead 810, or other lead, to a heart 815 of patient 820. Pacemaker 805 is adapted to perform the methods of adjusting output mapping as described herein. System 800 also includes an external programmer 825 providing wireless communication with pacemaker 805 using a telemetry device 830, such as might be used by a physician to initially program or periodically reprogram pacemaker 805. Endocardial lead 810 includes a proximal end 835, which is coupled to pacemaker 805, and a distal end 840, which is coupled to one or more portions of heart 815.

CONCLUSION

Methods of adjusting an output mapping in response to historical signal input have been described along with apparatus adapted to perform such methods. The methods include obtaining signal input data, generating historical signal input data indicative of a breadth and/or frequency of signal input data exceeding a reference value, and adjusting the output mapping in response to the historical signal input data. The methods provide for increasing the output mapping in response to increasing breadth and/or frequency of signal input values exceeding the reference value and decreasing the output mapping in response to decreasing breadth and/or frequency of signal input values exceeding the reference value. The methods are particularly adapted to aid approach of steady-state conditions in closed-loop systems. Apparatus adapted to perform the methods include a processor, a control output, a control input, a regulator for providing a signal to the control output in response to a signal received at the control input, and a memory for storing historical signal input data.

In particular, methods of adjusting rate-adaptive pacemakers in response to a patient's demonstrated activity have been described along with pacemakers adapted to perform such methods. The methods include using historical physiologic sensor input to derive a patient's activity level. The methods further include tuning a rate-adaptive curve in response to a patient's demonstrated activity level relative to a predetermined activity level. Pacemakers adapted to perform the methods include a processor, at least one physiologic sensor input, a variable-rate pulse generator and a memory for storing historical physiologic sensor data.

Although specific embodiments have been illustrated and described herein, it will be appreciated by those of ordinary skill in the art that any arrangement which is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of adjusting an at least two-slope rate-adaptive curve for pacing a patient's heart, the curve including at least one breakpoint between slopes, the method comprising:

sensing the patient's activity and producing sensed activity data therefrom;

generating a demonstrated activity level from the sensed activity data; and adjusting at least one of a slope and a breakpoint of the at least two-slope rate-adaptive curve in response to the demonstrated activity level relative to a predetermined activity level.

2. The method of claim 1, wherein sensing the patient's activity further comprises receiving input from at least one physiologic sensor.

3. The method of claim 1, wherein sensing the patient's activity further comprises receiving input from at least one physiologic sensor selected from the group consisting of minute ventilation sensors and accelerometers.

4. The method of claim 1, wherein adjusting the rate-adaptive curve further comprises increasing the rate-adaptive curve when the demonstrated activity level exceeds the predetermined activity level.

5. The method of claim 1, wherein adjusting the rate-adaptive curve further comprises decreasing the rate-adaptive curve when the demonstrated activity level is less than the predetermined activity level.

6. The method of claim 1, wherein the predetermined activity level corresponds to a prescribed exercise level and frequency.

7. A method of adjusting an at least two-slope rate-adaptive curve for pacing a patient's heart, the curve including at least one breakpoint between slopes, the method comprising:
  sensing the patient's activity having an exertion level;
  generating a factor indicative of a breadth of the patient's exertion levels above a predetermined exertion level; and
  adjusting at least one of a slope and a breakpoint of the at least two-slope rate-adaptive curve in response to the factor.

8. The method of claim 7, wherein the factor increases for increasing breadth of the patient's exertion levels above the predetermined exertion level.

9. A method of adjusting an at least two-slope output mapping of a control output versus a control input, the mapping including at least one breakpoint between slopes, the method comprising:
  obtaining signal input data, wherein the signal input data comprises data from the control input;
  generating historical signal input data from the signal input data, wherein the historical signal input data is indicative of a frequency of the signal input data in excess of a first reference value; and
  adjusting at least one of a slope and a breakpoint of the at least two-slope output mapping in response to the historical signal input data.

10. The method of claim 9, wherein adjusting the output mapping includes increasing an area of the output mapping in response to increasing values of the at least one factor.

11. The method of claim 1, further comprising:
  obtaining data from an auxiliary input;
  generating historical auxiliary input data from the auxiliary input data, wherein the historical auxiliary input data is indicative of at least one factor selected from the group consisting of a breadth and a frequency of the auxiliary input data in excess of a second reference value; and
  adjusting the output mapping in response to the historical auxiliary input data as well as the historical signal input data.

12. The method of claim 11, wherein the first reference value is for comparison to the data from the signal input, and the second reference value is for comparison to the data from the auxiliary input.

13. A method of adjusting an at least two-slope output mapping of a control output versus a control input, the mapping including at least one breakpoint between slopes, the method comprising:
  obtaining signal input data, wherein the signal input data comprises data from an auxiliary input;
  generating historical signal input data from the signal input data, wherein the historical signal input data is indicative of a frequency of the signal input data in excess of a reference value; and
  adjusting at least one of a slope and a breakpoint of the at least two-slope output mapping in response to the historical signal input data.

14. The method of claim 13, wherein adjusting the output mapping includes increasing an area of the output mapping in response to increasing values of the at least one factor.

15. A method of adjusting an at least two-slope rate-adaptive curve for pacing a patient's heart, the curve including at least one breakpoint between slopes, the method comprising:
  sensing the patient's activity and determining both an exertion level, and an exertion time at the exertion level;
  generating a first factor indicative of a breadth of the patient's exertion levels above a predetermined exertion level;
  generating a second factor indicative of the patient's exertion time at exertion levels above the predetermined exertion level; and
  adjusting at least one of a slope and a breakpoint of the at least two-slope rate-adaptive curve in response to the first and second factors.

16. The method of claim 15, wherein the first factor increases for increasing breadth of the patient's exertion levels above the predetermined exertion level.

17. The method of claim 15, wherein the second factor increases for increasing frequency of the patient's exertion levels above the predetermined exertion level.

18. A method of adjusting an at least two-slope output mapping of a control output versus a control input, the mapping including at least one breakpoint between slopes, the method comprising:
  obtaining signal input data, wherein the signal input data comprises data from the control input;
  generating historical signal input data from the signal input data;
  generating a first factor indicative of a breadth of the historical signal input data in excess of a reference value;
  generating a second factor indicative of a frequency of the historical signal input data in excess of the reference value; and
  adjusting at least one of a slope and a breakpoint of the output mapping in response to the first and second factors.

19. The method of claim 18, wherein adjusting the output mapping further comprises increasing an area of the output mapping in response to increasing values of the first factor and decreasing the area of the output mapping in response to decreasing values of the first factor.

20. The method of claim 18, wherein adjusting the output mapping further comprises increasing an area of the output mapping in response to increasing values of the second factor and decreasing an area of the output mapping in response to decreasing values of the second factor.

21. A method of adjusting an at least two-slope output mapping of a control output versus a control input, the mapping including at least one breakpoint between slopes, the method comprising:

obtaining signal input data, wherein the signal input data comprises data from an auxiliary input;

generating historical signal input data from the signal input data;

generating a first factor indicative of a breadth of the historical signal input data in excess of a reference value;

generating a second factor indicative of a frequency of the historical signal input data in excess of the reference value; and adjusting at least one of a slope and a breakpoint of the at least two-slope output mapping in response to the first and second factors.

22. The method of claim 21, wherein adjusting the output mapping further comprises increasing an area of the output mapping in response to increasing values of the first factor and decreasing the area of the output mapping in response to decreasing values of the first factor.

23. The method of claim 21, wherein adjusting the output mapping further comprises increasing an area of the output mapping in response to increasing values of the second factor and decreasing an area of the output mapping in response to decreasing values of the second factor.

24. A method of adjusting an at least two-slope output mapping of a control output versus a control input, the mapping including at least one breakpoint between slopes, the method comprising:

obtaining data from the control input, thereby producing control input data;

obtaining data from auxiliary input, thereby producing auxiliary input data;

generating historical control input data from the control input data;

generating historical auxiliary input data from the auxiliary input data;

generating a first factor indicative of a breadth of the historical control input data in excess of a first reference value and a breadth of the historical auxiliary input data in excess of a second reference value;

generating a second factor indicative of a frequency of the historical control input data in excess of the first reference value and a frequency of the historical auxiliary input data in excess of the second reference value; and adjusting at least one of a slope and a breakpoint of the at least two-slope output mapping in response to the first and second factors.

25. The method of claim 24, wherein adjusting the output mapping further comprises increasing an area of the output mapping in response to increasing values of the first factor and decreasing the area of the output mapping in response to decreasing values of the first factor.

26. The method of claim 24, wherein adjusting the output mapping further comprises increasing an area of the output mapping in response to increasing values of the second factor and decreasing an area of the output mapping in response to decreasing values of the second factor.

27. A method of adjusting a two-slope rate-adaptive curve for pacing a patient's heart, wherein the two-slope rate-adaptive curve is defined by variables of a heart rate at breakpoint, a sensor target rate, a high heart-rate response factor, a lower endpoint and an upper endpoint, the method comprising:

sensing the patient's activity having both an exertion level and an exertion time at the exertion level using at least one physiologic sensor input;

generating a first factor indicative of a breadth of the patient's exertion levels above a predetermined exertion level;

generating a second factor, indicative of the patient's exertion time at exertion levels above the predetermined exertion level; and adjusting the variables of the heart rate at breakpoint, the sensor target rate and the high heart-rate response factor in response to the first and second factors.

28. The method of claim 27, wherein adjusting the variables of the heart rate at breakpoint, the sensor target rate and the high heart-rate response factor occur with the lower and upper endpoints constrained.

29. A control system, comprising:

a processor;

a memory coupled to the processor and having first data stored thereon defining an at least two slope output mapping including at least one breakpoint between slopes;

a regulator coupled to the processor;

a control input coupled to the processor; and a control output coupled to the regulator;

wherein the processor is adapted to sample second data from the control input, store the sampled second data to the memory, generate historical signal input data indicative of a frequency of the second data in excess of a first reference value, and adjust at least one of a slope and a breakpoint of the at least two-slope output mapping in response to the historical signal input data.

30. A control system, comprising:

a processor;

a control input coupled to the processor;

a memory coupled to the processor and having first data stored thereon defining an at least two-slope output mapping including at least one breakpoint between slopes, wherein the output mapping is responsive to data from the control input;

a regulator coupled to the processor;

an auxiliary input coupled to the processor; and a control output coupled to the regulator;

wherein the processor is adapted to sample second data from the auxiliary input, store the sampled second data to the memory, generate historical signal input data indicative of a frequency of the second data in excess of a first reference value, and adjust at least one of a slope and a breakpoint of the at least two-slope output mapping in response to the historical signal input data.

31. A rate-adaptive pacemaker, comprising:

a processor;

a memory coupled to the processor;

a variable-rate pulse generator coupled to the processor; and at least one physiologic sensor input coupled to the processor;

wherein the memory has instructions stored thereon capable of causing the processor to perform a method, the method comprising:

storing first data to the memory defining an at least two-slope rate-adaptive curve including at least one breakpoint between slopes;

sampling second data from the at least one physiologic sensor input indicative of a patient's activity;

storing the sampled second data to the memory, and generating historical activity data indicative of a frequency of the second data in excess of a first reference value; and adjusting at least one of a slope and a breakpoint of the at least two-slope rate-adaptive curve in response to the historical activity data.

32. The rate-adaptive pacemaker of claim 31, wherein the at least one physiologic sensor is selected from the group consisting of minute ventilation sensors and accelerometers.

33. The rate-adaptive pacemaker of claim 31, wherein adjusting first data defining the rate-adaptive curve further comprises increasing the rate-adaptive curve when the patient's activity exceeds a predetermined activity level.

34. The rate-adaptive pacemaker of claim 33, wherein the predetermined activity level corresponds to a prescribed exercise level and frequency.

35. The rate-adaptive pacemaker of claim 31, wherein adjusting first data defining the rate-adaptive curve further comprises decreasing the rate-adaptive curve when the patient's activity is less than a predetermined activity level.

36. The rate-adaptive pacemaker of claim 35, wherein the predetermined activity level corresponds to a prescribed exercise level and frequency.

37. A rate-adaptive pacemaker, comprising:

a processor;

a memory coupled to the processor;

a variable-rate pulse generator coupled to the processor; and at least one physiologic sensor input coupled to the processor;

wherein the memory has instructions stored thereon capable of causing the processor to perform a method, the method comprising:

storing first data to the memory defining an at least two-slope rate-adaptive curve including at least one breakpoint between slopes;

sampling second data from the at least one physiologic sensor input indicative of a patient's activity having an exertion level;

storing the sampled second data to the memory, thereby generating historical activity data;

generating a factor indicative of a breadth of the patient's exertion levels above a predetermined exertion level; and adjusting at least one of a slope and a breakpoint of the at least two-slope rate-adaptive curve in response to the factor.

38. The rate-adaptive pacemaker of claim 37, wherein the factor increases for increasing breadth of the patient's exertion levels above the predetermined exertion level.

39. A rate-adaptive pacemaker, comprising:

a processor;

a memory coupled to the processor;

a variable-rate pulse generator coupled to the processor; and at least one physiologic sensor input coupled to the processor;

wherein the memory has instructions stored thereon capable of causing the processor to perform a method, the method comprising:

storing first data to the memory defining an at least two-slope rate-adaptive curve including at least one breakpoint between slopes;

sampling second data from the at least one physiologic sensor input indicative of a patient's activity having an exertion level and an exertion time at the exertion level;

storing the sampled second data to the memory, thereby generating historical activity data;

generating a first factor indicative of a breadth of the patient's exertion levels above a predetermined exertion level;

generating a second factor indicative of the patient's exertion time at exertion levels above the predetermined exertion level; and adjusting at least one of a slope and a breakpoint of the at least two-slope rate-adaptive curve in response to the first and second factors.

40. The rate-adaptive pacemaker of claim 39, wherein the first factor increases for increasing breadth of the patient's exertion levels above the predetermined exertion level.

41. The rate-adaptive pacemaker of claim 39, wherein the second factor increases for increasing frequency of the patient's exertion levels above the predetermined exertion level.

42. A control system, comprising:

a processor;

a memory coupled to the processor;

a regulator coupled to the processor;

a control input coupled to the processor;

at least one auxiliary input coupled to the processor; and a control output coupled to the regulator;

wherein the memory has instructions stored thereon capable of causing the processor to perform a method, the method comprising:

storing first data to the memory defining an at least two-slope output mapping including at least one breakpoint between slopes;

sampling second data from the control input;

storing the sampled second data to the memory, thereby generating historical control input data;

sampling third data from the at least one auxiliary input;

storing the sampled third data to the memory, thereby generating historical auxiliary input data;

generating a first factor indicative of a breadth of the historical control input data above a first reference value and a breadth of the historical auxiliary input data above a second reference value;

generating a second factor indicative of a frequency of the historical control input data above the first reference value and a frequency of the historical auxiliary input data above the second reference value;

increasing the output mapping in response to increasing values of the first factor and decreasing the output mapping in response to decreasing values of the first factor; and increasing the output mapping in response to increasing values of the second factor and decreasing the output mapping in response to decreasing values of the second factor.

* * * * *

UNITED STATES PATENT AND TRADEMARK OFFICE
CERTIFICATE OF CORRECTION

PATENT NO.   : 6,490,485 B1                                                Page 1 of 1
DATED        : December 3, 2002
INVENTOR(S)  : Bruce H. KenKnight, Douglas J. Lang and Weimin Sun It is certified that error appears in the above-identified patent and that said Letters Patent is hereby corrected as shown below:

<u>Column 13,</u>
Line 53, delete "claim 1" and insert -- claim 9 -- therefor.

Signed and Sealed this

Twenty-ninth Day of July, 2003

JAMES E. ROGAN
*Director of the United States Patent and Trademark Office*